US012636156B2

(12) United States Patent
Vogt et al.

(10) Patent No.: US 12,636,156 B2
(45) Date of Patent: May 26, 2026

(54) AUGMENTATION DEVICE, COMPOSITE AND METHOD FOR PRODUCING A COMPOSITE

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 768 days.

(21) Appl. No.: 18/064,056

(22) Filed: Dec. 9, 2022

(65) Prior Publication Data

US 2023/0190479 A1 Jun. 22, 2023

(30) Foreign Application Priority Data

Dec. 17, 2021 (EP) .................................... 21215423

(51) Int. Cl.
*A61F 2/30* (2006.01)
*A61L 27/16* (2006.01)
(52) U.S. Cl.
CPC ...... *A61F 2/30734* (2013.01); *A61F 2/30771* (2013.01); *A61L 27/16* (2013.01); *A61F 2002/30331* (2013.01); *A61F 2002/30403* (2013.01); *A61F 2002/30467* (2013.01); *A61F*

*2002/30736* (2013.01); *A61F 2002/30784* (2013.01); *A61F 2002/3092* (2013.01); *A61L 2430/02* (2013.01)

(58) Field of Classification Search
CPC .. A61F 2002/30116; A61F 2002/30622; A61F 2002/2835; A61F 2002/30225; A61F 2002/30736; A61F 2/30734; A61F 2002/30462; A61F 2002/4415; A61F 2220/0075; A61F 2002/30403
See application file for complete search history.

(56) References Cited

U.S. PATENT DOCUMENTS

2006/0265077 A1* 11/2006 Zwirkoski ............... A61F 2/442
623/17.14
2016/0331540 A1* 11/2016 Vogt ........................ A61P 19/00

FOREIGN PATENT DOCUMENTS

EP 3092076 B1 4/2019
WO 2013074909 A1 5/2013

* cited by examiner

*Primary Examiner* — Javier G Blanco
(74) *Attorney, Agent, or Firm* — Dicke, Billig & Czaja, PLLC

(57) ABSTRACT

Augmentation material having a wire and, in axial alignment along the wire, a plurality of groups of axially adjacent connecting elements that extend radially from the wire, wherein the connecting elements are designed such that, when a first group from the plurality of groups is pressed together with a further group from the plurality of groups, the connecting element of the two groups can be connected to one another in a positive-locking and/or friction-locking manner.

10 Claims, 12 Drawing Sheets

AUGMENTATION DEVICE, COMPOSITE AND METHOD FOR PRODUCING A COMPOSITE

CROSS-REFERENCE TO RELATED APPLICATIONS

This application claims priority pursuant to 35 U.S.C. 119(a) to European Application No. 21215423.1, filed Dec. 17, 2021, which application is incorporated herein by reference in its entirety.

DESCRIPTION

The invention relates to an augmentation material having a wire and, in axial alignment along the wire, a plurality of groups of axially adjacent connecting elements that extend radially from the wire, wherein the connecting elements are designed such that, when a first group from the plurality of groups is pressed together with a further group from the plurality of groups, the connecting element of the two groups can be connected to one another in a positive-locking and/or friction-locking manner.

The invention further relates to a composite comprising the augmentation material and a bone cement and to a method for producing a composite.

The subject matter of the invention is in particular an alloplastic augmentation material for use in articular endoprostheses operations, in particular revision articular endoprostheses operations. The augmentation material according to the invention is intended for filling and stabilizing cavities, in particular bone cavities, such as a bone canal. For this purpose, the augmentation material can be formed as a composite with a bone cement.

BACKGROUND OF THE INVENTION

Augmentation materials have been known for a long time and are used extensively clinically (J. M. Rueger: Knochenersatzmittel [Bone Replacement Materials], Orthopade [Orthopedics] 27 (1998) 72-79.). The augmentation materials used to date are generally stable in volume but are not dimensionally stable. One exception is constituted by an augmentation material sold under the name "Trabecular Metal™" from Zimmer and is known, for example, from WO 2013/074 909 A1. This material has a porous structure that mimics the structure of the human spongiosa (spongy tissue). This material comprises tantalum and is commercially available in defined shapes and sizes. The material cannot be changed in its shape and size in the operating room and cannot be machined using conventional tools in the operating room. The particular anatomical situation of the patient can only be taken into account, therefore, to a limited extent. The medical user can only attempt to adapt implant sites of the patient to the predetermined geometry or to use an approximately fitting implant and to close the existing gaps with allogeneic bone material or other volume fillers.

The patent specification EP 3 092 076 B1 describes a particulate alloplastic augmentation material for producing a freely shaped porous body. For this purpose, when the particles are pressed together, the individual particles of the augmentation material engage in one another in such a way that a freely shapable porous body is produced, which can subsequently be filled with a bone cement in order to produce a composite. A disadvantage of a particulate augmentation material is that it is unsafe to use during an operation. For example, care must be taken to ensure that the particles do not unintentionally end up in undesired locations in the patient's body, which can hinder the course of the operation or, in the worst case, can lead to health complications in the patient. In addition, the formation of the freely shaped porous body from a particulate material is time-consuming, which is disadvantageous especially in time-critical operations. Loose particles, especially loose particles falling on the operating room floor, moreover represent a not inconsiderable accident potential.

Objects

It is an object of the present invention to at least partially overcome one or more of the disadvantages resulting from the prior art.

In particular, an augmentation material is to be provided which can easily, quickly and safely be freely shaped and is suitable for filling bone cavities. The augmentation material should be able to follow the contour of the cavity. After forming, the augmentation material should form a stable porous body without chemical curing reactions, such as radical polymerizations, being necessary. After forming, the bone replacement material should have an open porosity and be mechanically stable. The porosity and the size of the pores should be sufficient and suitable for the purpose that human bone of a patient who is treated with the bone replacement material can grow into the pores. Furthermore, the pores should be suitable for being stabilized by infiltration with a bone cement paste, in particular with a PMMA bone cement paste. The augmentation material should be able to form a pressure-stable composite with the bone cement. In this case, overheating of the composite during the curing of the bone cement paste, in particular of the PMMA bone cement paste, resulting in damage to the tissue of the patient should be avoided. The volume of the augmentation material should be machinable with tools available in operating rooms, such as shears or pliers.

It is a further object of the invention to provide a composite which can be produced easily, quickly and in a freely shapable manner using the augmentation material and which avoids limitations of conventional composites.

A further aim of the invention is to provide a method for producing a composite which avoids limitations of traditional methods for producing a composite.

Preferred Embodiments of the Invention

A contribution to at least partially achieving at least one of the aforementioned objects is made by the features of the independent claims. The dependent claims provide preferred embodiments that contribute to at least partially achieving at least one of the objects.

A first embodiment of the invention is an augmentation material comprising a wire and, in axial alignment along a longitudinal axis of the wire, a plurality of groups of axially adjacent connecting elements that extend radially from the wire, wherein the connecting elements are designed such that, when a first group from the plurality of groups is pressed together with a further group from the plurality of groups, the connecting elements of the two groups can be connected to one another in a positive-locking and/or friction-locking manner.

In one embodiment of the augmentation material, axially adjacent connecting elements in a group have an axial connecting element spacing from one another which corresponds to at least one axial connecting element extension of a connecting element along the longitudinal axis of the wire. This embodiment is a second embodiment of the invention, which is preferably dependent on the first embodiment of the invention.

In one embodiment of the augmentation material, the connecting elements are formed as disks that extend radially from the wire. This embodiment is a third embodiment of the invention, which is preferably dependent on the first or second embodiment of the invention.

In one embodiment of the augmentation material, the disks are perforated, the disks have an open-pore structure or the disks are perforated and have an open-pore structure. This embodiment is a fourth embodiment of the invention, which is preferably dependent on the third embodiment of the invention.

In one embodiment of the augmentation material, the connecting elements are formed as pins that extend radially from the wire. This embodiment is a fifth embodiment of the invention, which is preferably dependent on the first or second embodiment of the invention.

In one embodiment of the augmentation material, a plurality of pins, in particular 4 to 10, preferably 4 to 8, more preferably 6 to 8, extend radially adjacently from the wire. This embodiment is a sixth embodiment of the invention, which is preferably dependent on the fifth embodiment of the invention.

In one embodiment of the augmentation material, the pins extend radially from the wire with a pin length that corresponds to at least three times a wire diameter of the wire. This embodiment is a seventh embodiment of the invention, which is preferably dependent on the fifth or sixth embodiment of the invention.

In one embodiment of the augmentation material, the pins comprise mushrooms, hooks, loops, undercuts and/or latching elements; preferably the pins are formed as mushrooms, hooks, loops, undercuts and/or latching elements. This embodiment is an eighth embodiment of the invention, which is preferably dependent on the fifth to eighth embodiment of the invention.

In one embodiment of the augmentation material, a group of connecting elements comprises 3 to 20, preferably 3 to 15, more preferably 5 to 15, axially adjacent connecting elements. This embodiment is a ninth embodiment of the invention, which is preferably dependent on any of the preceding embodiments of the invention.

In one embodiment of the augmentation material, axially adjacent groups of connecting elements, in particular directly axially adjacent groups of connecting elements, have an axial group spacing from one another which corresponds to at least twice the axial extension of a connecting element along the longitudinal axis of the wire. This embodiment is a tenth embodiment of the invention, which is preferably dependent on any of the preceding embodiments of the invention.

In one embodiment of the augmentation material, the augmentation material is produced using a generative 3D printing method. This embodiment is an eleventh embodiment of the invention, which is preferably dependent on any of the preceding embodiments of the invention.

A twelfth embodiment of the invention is a composite comprising an augmentation material according to any of the preceding embodiments of the invention and a bone cement, in particular a PMMA bone cement, wherein the augmentation material is encased, in particular completely encased, in the bone cement, in particular in the PMMA bone cement.

In one embodiment of the composite, the augmentation material in the composite occupies a volume fraction in the range of 30-70 percent by volume relative to the volume of the composite. This embodiment is a thirteenth embodiment of the invention, which is preferably dependent on the twelfth embodiment of the invention.

A fourteenth embodiment of the invention is a method for producing a composite, in particular a composite according to the twelfth or thirteenth embodiment of the invention, for filling a cavity, in particular a cavity in a bone, in particular a bone canal, comprising the steps of a. providing the augmentation material in an arrangement substantially corresponding to the shape of the cavity;

b. applying a bone cement paste into interspaces of the augmentation material such that the augmentation material is completely encased in the bone cement paste; and c. curing the bone cement paste to form the composite.

In one embodiment of the method, the augmentation material is provided in the cavity to be filled, and the application of the bone cement paste into the interspaces of the augmentation material and the curing of the bone cement paste takes place in the cavity.

General

In the present description, range indications also include the values specified as limits. An indication of the type "in the range from X to Y" with respect to a variable A therefore means that A can assume the values X, Y and values between X and Y. Ranges delimited on one side of the type "up to Y" for a variable A accordingly mean value Y and less than Y.

Some of the described features are linked to the term "substantially". The term "substantially" is to be understood as meaning that, under real conditions and manufacturing techniques, a mathematically exact interpretation of terms such as "superimposition", "perpendicular", "diameter" or "parallelism" can never be given exactly, but only within certain manufacturing-related error tolerances. For example, "substantially perpendicular axes" form an angle of 85 degrees to 95 degrees relative to one another, and "substantially equal volumes" comprise a deviation of up to 5% by volume. A "device consisting substantially of plastics material" comprises, for example, a plastics material fraction of $\geq 95$ to $\leq 100\%$ by weight. A "substantially complete filling of a volume B" comprises, for example, a filling of $\geq 95$ to $\leq 100\%$ by volume of the total volume of B.

DETAILED DESCRIPTION

A first subject of the invention relates to an augmentation material comprising a wire and, in axial alignment along a longitudinal axis of the wire, a plurality of groups of axially adjacent connecting elements that extend radially from the wire, wherein the connecting element are designed such that, when a first group from the plurality of groups is pressed together with a further group from the plurality of groups, the connecting elements of the two groups, that is to say the first group and the further group from the plurality of groups, can be connected to one another in a positive-locking or friction-locking manner or in a positive-locking and friction-locking manner.

The augmentation material comprises a wire. Wire is understood to mean a plastically deformable elongate body. The wire can be formed in one piece or can also be composed of a plurality of, for example two to ten, wire part elements, optionally with one or more additional inserts. For example, the wire can be composed of a plurality of wire part elements which are twisted and/or braided. Due to the simple production, a one-piece wire is preferred.

The wire can have different cross-sectional geometries, such as, for example, angular, in particular quadrilateral or hexagonal, oval or star-shaped cross-sectional geometries, wherein round cross-sectional geometries are preferred due to the simpler production method.

The wire diameter of the wire is preferably in the range from 0.1 mm to 2 mm, more preferably in the range from 0.2 mm to 1.5 mm. On the one hand, this allows easy deformation of the wire, and thus of the augmentation material, into the desired shape and, on the other hand, maintains a certain stability of the porous body formed in this way from the augmentation material.

In addition, such a wire diameter allows a simple shortening of the wire, and thus of the augmentation material, with tools present in an operating room, such as pliers or shears.

The wire preferably has a wire length which in the range from 10 cm to 50 cm, more preferably in the range from 10 cm to 40 cm. This allows the filling of common cavity sizes in the course of an operation.

A plurality of groups of axially adjacent connecting elements extend radially from the wire, at an angle in a range of 60°-120° relative to the longitudinal axis of the wire.

A connecting element is understood to mean a structural projection on the outer surface of the wire. In one embodiment, the wire and the connecting elements are connected to one another in a positive-locking and/or friction-locking manner. In a further embodiment, the wire and the connecting elements are integrally bonded to one another. In a further preferred embodiment, the wire and the connecting elements are formed in one piece, wherein the outer surface of the wire itself is formed as the plurality of connecting elements. The latter is preferred due to the simpler and more cost-effective production method.

Connecting elements are axially adjacent when they are arranged at or on different positions along the longitudinal axis of the wire.

The connecting elements are arranged in a plurality of groups, i.e., at least two groups, wherein one group comprises at least a plurality of, i.e., at least two, adjacent connecting elements arranged axially along the longitudinal axis of the wire. The plurality of groups of connecting elements can be arranged relative to one another in such a way that they appear to be a single large group of connecting elements.

In this case, the connecting elements are formed in such a way that two groups of connecting elements are pressed together to form a positive-locking connection, a friction-locking connection or a positive-locking and friction-locking connection between the connecting elements of the two groups. The connecting elements of the groups engage in one another in order to form a positive-locking and/or friction-locking connection. The pressing together of two groups of connecting elements can be made possible, for example, by deforming the wire. For example, the wire can be bent or wound such that the two groups of connecting elements are connected to one another at the two axially opposite ends of the wire, and thus of the augmentation material. In one embodiment, the connection of the groups is reversible, so that they can be detached from one another again. In a further embodiment, the connection is irreversible, so that it cannot be released again in a destruction-free manner.

By means of the flexible wire, the augmentation material can be introduced into any shaped porous body, in particular for filling bone cavities, quickly, easily and safely. The connecting elements thus enable the porous body shaped in this way to be stabilized without the augmentation material automatically moving back into its original shape. The augmentation material brought into shape in this way forms a porous body, wherein the pores of the porous body are the interspaces of the connecting elements and of the wire brought into shape.

Because the augmentation material is formed in one piece, it can be used safely in the course of an operation.

In order to adapt the augmentation material to the size of the cavity to be filled, the wire can be shortened at any point, in particular between axially adjacent connecting elements. Depending on the material used for the wire, this can be accomplished, for example, using shears or pliers.

The axial connecting element spacing, i.e., the axial spacing between two axially adjacent connecting elements in a group, can assume different values. Due to the simpler production method, all connecting elements in a group have the same axial connecting element spacing.

In one embodiment of the augmentation material, axially adjacent connecting elements in a group have an axial connecting element spacing from one another which corresponds to at least one axial connecting element extension of a connecting element along the longitudinal axis of the wire. The axial connecting element spacing is understood to mean the spacing between two connecting elements that runs in parallel with the longitudinal axis of the wire at the level of the wire.

The connecting elements can be formed with uneven thickness over their radial extension, which runs substantially perpendicularly to the longitudinal axis of the wire. For example, the connecting elements can have directly adjacently to the wire an axial extension, which is reduced with increasing radial spacing from the wire. For example, this is the case with connecting elements which are designed as discus-like disks formed concentrically around the wire. The axial connecting element extension is to be understood to mean the axial extension of the part of the connecting element having the greatest radial spacing from the wire.

Preferably, the axial connecting element spacing has a value which lies in a range of 1 to 2 times, preferably 1.05 to 1.8 times, the value of the axial connecting element extension. This enables a simple insertion of a connecting element of a first group between two axially adjacent connecting elements of a further group of connecting elements, forming a positive-locking and/or friction-locking connection between the connecting elements. In particular, a precisely fitting positive-locking connection between connecting elements pressed together can be formed, for example, when the axial connecting element spacing corresponds to the axial connecting element extension. If the axial connecting element spacing has a value less than 1 times the axial connecting element extension, the formation of a positive-locking and/or friction-locking connection between the connecting elements that are pressed together is made more difficult. If the axial connecting element spacing has a value greater than 2 times the axial connecting element extension, in particular the holding force of the friction-locking connection of the pressed together connecting elements and the porous body formed from the augmentation material loses stability.

Preferably, the connecting elements have an axial connecting element extension in a range from 0.05 mm to 1.5 mm, preferably in a range from 0.5 to 1 mm, in order to ensure good handling of the augmentation material.

The connecting elements can be shaped differently in order to form a positive-locking and/or friction-locking connection when they are pressed together.

In one embodiment of the augmentation material, the connecting elements are formed as disks that extend radially from the wire. Due to the simple production method and greater ease of use, it is preferred that the disks are arranged substantially concentrically around the wire. The disk-shaped connecting elements allow pressing together over the full radial circumference of the wire, so that a high variation of shaped porous bodies is easily accessible by means of the augmentation material.

The disks can have differently shaped cross-sectional geometries. For example, the disks can have an elliptical, angular, in particular quadrilateral, pentagonal or hexagonal, wherein disks having a round cross-sectional geometry are preferred due to the simpler production method.

The connecting elements designed as disks can have a closed, smooth surface structure.

In one embodiment of the augmentation material, the connecting elements formed as disks are perforated and thus comprise one or more openings in the axial direction along the longitudinal axis of the wire. In one embodiment, the connecting elements formed as disks have an open-pore structure. In one embodiment, the connecting elements formed as disks are perforated and have an open-pore, sponge-like structure. The aforementioned embodiments allow improved ingrowth of newly formed bone tissue, both into the interspaces of the shaped porous body and, thus, into the interspaces between the wire and the disks, as well as into the perforations and/or into the open-pore structure of the individual disks. In addition, a toothing with bone cement is improved by such connecting elements.

In one embodiment of the augmentation material, the connecting elements are formed as pins that extend radially from the wire. Pins are understood to mean elongate structural units whose longitudinal axis forms an angle with the longitudinal axis of the wire in the range from 60° to 120°. Because of the simple production, it is preferred if the longitudinal axis of the pins and the longitudinal axis of the wire are substantially perpendicular to one another. It is preferred for all pins to have the same pin length and the same pin diameter.

The pins can be arranged on the wire such that each pin comprises one or two axially adjacent pins, so that at most one pin is arranged on each given cross-sectional plane of the wire. For example, all pins can point in the same direction as seen from the wire, as is the case, for example, with teeth of a comb starting from the handle thereof.

In one embodiment, a plurality of pins, in particular 4 to 10, preferably 6 to 8, extend radially adjacently from the wire. A plurality of pins, in particular 4 to 10, preferably 6 to 8, are thus arranged in the corresponding cross-sectional planes of the wire. The radially adjacent pins extend from the wire in a disk-like or star-shaped manner substantially in one plane. This enables an improved positive-locking and/or friction-locking connection for pins of different groups of connecting elements that are pressed together. In particular, the groups of connecting elements can be connected to one another in a positive-locking and/or friction-locking manner from variable directions and angles, so that the user of the augmentation material has more freedom in his/her design of the porous body formed from the augmentation material.

The pins can be formed having different lengths in order to form a positive-locking and/or friction-locking connection to one another.

In one embodiment of the augmentation material, the pins extend radially from the wire with a pin length that corresponds to at least three times the wire diameter of the wire. This allows the formation of a porous body from the augmentation material that is as stable as possible. In order not to impede the handling of the augmentation material, it is preferred if the pin length does not correspond to more than ten times the wire diameter.

The pins can have different cross-sectional geometries such as, for example, angular, in particular quadrilateral, pentagonal or hexagonal, oval or round cross-sectional geometries, wherein a round cross-sectional geometry is preferred due to the simpler production method. In particular, the pins can be cylindrical in shape, wherein the pin end facing away from the wire can have a polygonal or round, in particular hemispherical, shape.

In order to further improve the positive-locking and/or friction-locking connection of the pins when second groups of pins are pressed together, the pins in one embodiment of the augmentation material comprise mushrooms—i.e., mushroom-shaped, substantially hemispherical, structural units protruding beyond the actual pin diameter—hooks, loops, undercuts and/or latching elements, or the pins are formed as mushrooms, hooks, loops, undercuts and/or latching elements.

For example, the pins can be provided with mushrooms, i.e., mushroom-shaped structural units, in particular on the pin end opposite the wire, so that the mushrooms of the pins from different groups that are pressed together snap together in a barb-like manner together and thus form the connection of the pins more stably than would be the case without mushrooms.

In one embodiment of the augmentation material, a group of connecting elements comprises 3 to 20, preferably 3 to 15, more preferably 5 to 15, axially adjacent connecting elements.

For example, a group of connecting elements comprises 10 axially adjacent disks. In addition to the axially adjacent connecting elements, particularly in the case of connecting elements in the form of pins, the axially adjacent connecting elements can comprise additional radially adjacent connecting elements. For example, a group can comprise 10 axially adjacent pins, wherein each of these 10 axially adjacent pins comprises, in each case, an additional 5 radially adjacent pins which each lie substantially in the same cross-sectional plane of the wire as the corresponding axially adjacent pins. Such a group of connecting elements thus comprises a total of 60 pins.

The groups of connecting elements may be so close together axially that they appear to be one large group of connecting elements.

In one embodiment of the augmentation material, axially adjacent groups of connecting elements have an axial group spacing from one another which corresponds to at least twice the axial extension of a connecting element along the longitudinal axis of the wire. The axial group spacing is understood to mean the spacing between two groups of connecting elements that runs in parallel with the longitudinal axis of the wire.

This enables improved flexibility of the wire and at the same time ensures that the porous body formed from the augmentation material has a higher number of and larger pores, which allows improved ingrowth of bone tissue into the porous body and/or improved penetration of bone cement paste into the porous body.

The augmentation material can be produced in different ways.

In one embodiment of the augmentation material, the augmentation material is produced using a generative 3D printing method.

One particularly preferred example of a 3D printing method is selective laser melting (SLM). Other rapid prototyping methods or computer-assisted generative production methods can also be used to produce the augmentation material, such as fused layer modeling/manufacturing (FLM), fused deposition modeling (FDM), laminated object modeling (LOM) of plastics films, layer laminated manufacturing (LLM) of plastics films, electron beam melting (EBM) of plastics materials or metals, multi jet modeling (MJM) of plastics materials, selective laser sintering (SLS) of plastics materials or metals, and stereolithography (STL or SLA).

The augmentation material can comprise different materials or consist of different materials. For example, the augmentation material can be formed from biocompatible plastics material, stainless steel, titanium, a titanium alloy, tantalum, a tantalum alloy or from composites of these materials.

These materials can be used especially well for medical purposes, and suitable elastic properties for the connecting elements can also be set with these materials. Augmentation materials consisting of metal or metal alloys can preferably be produced by selective laser sintering or also by melting with electron beams, preferably with a 3D printing method.

The biocompatible plastics material can be biodegradable. For this purpose, polylactide, polylglycolide, polycaprolactone and polyester, which are formed from different a-hydroxycarboxylic acids, can be used. Polyamides, polyimides, polyetherketone and polysulfone are suitable as non-biodegradable plastics materials. Augmentation materials made from these non-biodegradable and degradable plastics materials can be produced by selective laser sintering.

A further subject of the invention relates to a composite comprising an augmentation material according to any of the preceding embodiments and a bone cement, in particular a PMMA bone cement, wherein the augmentation material is encased, in particular completely encased, in the bone cement.

To produce the composite, the augmentation material is encased, in particular completely encased, in a bone cement paste, which then cures to form a bone cement.

Bone cement paste is understood to mean a substance which is suitable in the field of medical technology to create a stable connection between artificial joints, such as hip and knee joints, for example, and bone material and/or to stabilize vertebral bodies. By curing, a bone cement is produced from a bone cement paste. These bone cements are preferably polymethyl methacrylate bone cements (PMMA bone cements) or inorganic bone cements.

PMMA bone cements have been used for a long time in medical applications and go back to work by Sir Charnley (cf. Charnley, J., Anchorage of the femoral head prosthesis of the shaft of the femur. *J. Bone Joint Surg.* 1960; 42, 28-30.). PMMA bone cements can be produced from a powder component comprising a bone cement powder as the first starting component and a liquid component comprising a monomer liquid as the second starting component. With a suitable composition, the two starting components can be storage-stable separately from one another. When the two starting components are brought into contact, a plastically deformable bone cement paste is produced by moisture expansion of the polymer components of the bone cement powder. In this case, polymerization of the monomer is initiated by radicals. As the polymerization of the monomer progresses, the viscosity of the bone cement paste increases until it cures completely.

Bone cement powder is understood to mean a powder which comprises at least a particulate polymethyl methacrylate and/or a particulate polymethyl methacrylate copolymer. Examples of copolymers are styrene and/or methyl acrylate. In one embodiment, the bone cement powder can additionally comprise a hydrophilic additive, which supports the distribution of the monomer liquid within the bone cement powder. In a further embodiment, the bone cement powder can additionally comprise an initiator which initiates the polymerization. In a further embodiment, the bone cement powder can additionally comprise a radiopaque material. In yet a further embodiment, the bone cement powder can additionally comprise pharmaceutically active substances such as antibiotics, for example.

The bone cement powder preferably comprises, as a hydrophilic additive, at least a particulate polymethyl methacrylate and/or a particulate polymethyl methacrylate copolymer, an initiator and a radiopaque material, or consists of these components. More preferably, the bone cement powder comprises at least a particulate polymethyl methacrylate and/or a particulate polymethyl methacrylate copolymer, an initiator, a radiopaque material, and a hydrophilic additive, or consists of these components. Most preferably, the bone cement powder comprises at least a particulate polymethyl methacrylate and/or a particulate polymethyl methacrylate copolymer, an initiator, a radiopaque material, a hydrophilic additive and an antibiotic, or consists of these components.

According to the invention, the particle size of the particulate polymethyl methacrylate and/or the particulate polymethyl methacrylate copolymer of the bone cement powder of the sieve fraction can correspond to less than 150 μm, preferably less than 100 μm.

According to the invention, the hydrophilic additive can be in particulate and/or fibrous form. In a further embodiment, the hydrophilic additive can be poorly soluble, preferably insoluble, in methyl methacrylate. In a further embodiment, the hydrophilic additive can have an absorption capacity of at least 0.6 g methyl methacrylate per gram of hydrophilic additive. In a further embodiment, the hydrophilic additive can comprise a chemical substance with at least one OH group. It can preferably be provided that the hydrophilic additive has covalently bonded OH groups on its surface. Examples of such preferred hydrophilic additives can be additives selected from the group comprising cellulose, oxycellulose, starch, titanium dioxide and silicon dioxide, wherein pyrogenic silicon dioxide is particularly preferred. In one embodiment, the particle size of the hydrophilic additive can correspond to the sieve fraction of less than 100 μm, preferably less than 50 μm and most preferably less than 10 μm. The hydrophilic additive can be contained in an amount of 0.1 to 2.5% by weight relative to the total weight of the bone cement powder.

According to the invention, the initiator can contain dibenzoyl peroxide or consist of dibenzoyl peroxide.

According to the invention, a radiopaque material is understood to mean a substance which makes it possible for the bone cement to be visible to X-ray diagnostic images. Examples of radiopaque material can comprise barium sulfate, zirconium dioxide and calcium carbonate.

According to the invention, the pharmaceutically active substance can comprise one or more antibiotics and, where applicable, added co-factors for the one or more antibiotics. Preferably, the pharmaceutically active substance consists of one or more antibiotics and, where applicable, added co-factors for the one or more antibiotics. Examples of antibiotics include gentamicin, clindamycin and vancomycin.

According to the invention, the monomer liquid can comprise the monomer methyl methacrylate or consist of methyl methacrylate. In one embodiment, the monomer liquid comprises, in addition to the monomer, an activator dissolved therein, such as N,N-dimethyl-p-toluidine, for example, or consists of methyl methacrylate and N,N-dimethyl-p-toluidine.

An inorganic bone cement is understood to mean a bone cement based on calcium phosphates and calcium sulfate dihydrate. Powder components used are powders of calcium phosphates and/or calcium sulfate dihydrate, which can be cured by a liquid component comprising an aqueous solution of different salts. A number of inorganic bone cements have been described, of which the following are mentioned by way of example: EP 1 592 463 B1, EP 2 271 585 B1 and EP 2 988 789 B1.

The bone cement fills, in particular, interspaces of the porous body formed from the augmentation material.

The composite forms a pressure-stable, non-porous body into which no bone tissue can grow.

The composite can have different volume fractions of augmentation material relative to bone cement.

In one embodiment of the composite, the augmentation material in the composite occupies a volume fraction in the range from 30 percent by volume to 70 percent by volume, preferably a volume fraction of 35 percent by volume to 65 percent by volume relative to the volume of the composite. Due to the volume fraction of at least 30 percent by volume of augmentation material, the composite can be produced by means of a bone cement paste, in particular a PMMA bone cement paste, without the bone cement paste, in particular the PMMA bone cement paste, heating during the curing of the bone cement paste in such a way that surrounding patient tissue can be thermally damaged. The structural stability of the composite decreases at volume fractions of more than 70 percent by volume of augmentation material.

A further subject of the invention relates to a method for producing a composite according to the invention, comprising the steps of a. providing the augmentation material in an arrangement substantially corresponding to the shape of the cavity;

b. applying a bone cement paste into interspaces of the augmentation material such that the augmentation material is completely encased in the bone cement paste; and c. curing the bone cement paste to form the composite.

In one step of the method, the augmentation material is provided. The provision of the augmentation material in an arrangement substantially corresponding to the shape of the cavity can be carried out in different ways. For example, the augmentation material can be wound spirally around an implant shaft of an implant, for example a hip joint endoprosthesis, which is to be inserted into a bone canal. The augmentation material substantially forms the contour of the corresponding bone canal and serves to fill the interspace between the implant and the wall of the bone canal. The augmentation material can be arranged in such a way that its groups of connecting elements are connected to one another in a positive-locking and/or friction-locking manner. This simplifies providing the augmentation material, because, for example, the stability of the shaped body made of the augmentation material is increased. Excess, unneeded augmentation material can easily be removed by shortening the wire, for example with shears or pliers. Should the wire of the augmentation material used not be long enough, a further augmentation material can be connected to the original wire quickly and easily by pressing the respective connecting elements together.

When providing the augmentation material substantially in the form of the cavity, it forms a stable porous body.

The interspaces of the augmentation material, i.e., the spaces between the shaped wire, the unbonded and interconnected connecting elements, are filled in a further step by applying a bone cement paste, in particular a PMMA bone cement paste, in such a way that the augmentation material is substantially completely encased in the bone cement paste. The porous body formed from the augmentation material is substantially completely filled with bone cement paste and encased therein.

In a further step of the method, the bone cement paste is cured to form the composite.

The method can be carried out completely outside the cavity to be filled.

In one embodiment of the method, the augmentation material is provided in the cavity to be filled, and both the application of the bone cement paste into the interspaces of the augmentation material and the curing of the bone cement paste take place in the cavity to be filled.

For example, the augmentation material is provided in a bone canal by it being wound in a spiral manner following the contour of the bone canal. Groups of connecting elements are thus preferably pressed together in order to form a stable porous body, in particular in the form of a hollow cylinder. In a further step, this porous body is filled within the bone canal with a bone cement paste such that the porous body is substantially completely encased in the bone cement paste. Before the bone cement paste cures, a corresponding implant is inserted into the bone canal in such a way that a shaft of the implant is surrounded by the augmentation material. The bone cement paste is then cured to form the composite.

The features and feature combinations disclosed for the augmentation material are also disclosed for the composite and the method and vice versa.

FIGURES

The invention is illustrated further in the following by way of example using figures. The invention is not limited to the figures.

In the figures:

FIG. 1 is a schematic top view of a portion of an augmentation material having a plurality of groups of connecting elements, FIG. 2 shows the augmentation material from FIG. 1 in a perspective side view, FIG. 3 is a further schematic top view of the augmentation material from FIGS. 1 and 2 with connected groups of connecting elements, FIG. 4 shows a further embodiment of an augmentation material in a schematic top view, FIG. 5 shows the augmentation material from FIG. 4 in a perspective side view, FIG. 6 shows a further embodiment of an augmentation material in a schematic top view, FIG. 7 shows the augmentation material from FIG. 6 in a perspective side view, FIG. 8 is a further schematic top view of the augmentation material from FIGS. 6 and 7 with connected groups of connecting elements, FIG. 9 shows a further embodiment of an augmentation material in a perspective side view, FIG. 10 shows a further embodiment of an augmentation material in a perspective side view, FIG. 11 shows a further embodiment of an augmentation material in a perspective side view, and FIG. 12 is a flowchart of a method for producing a composite.

Figure 1:
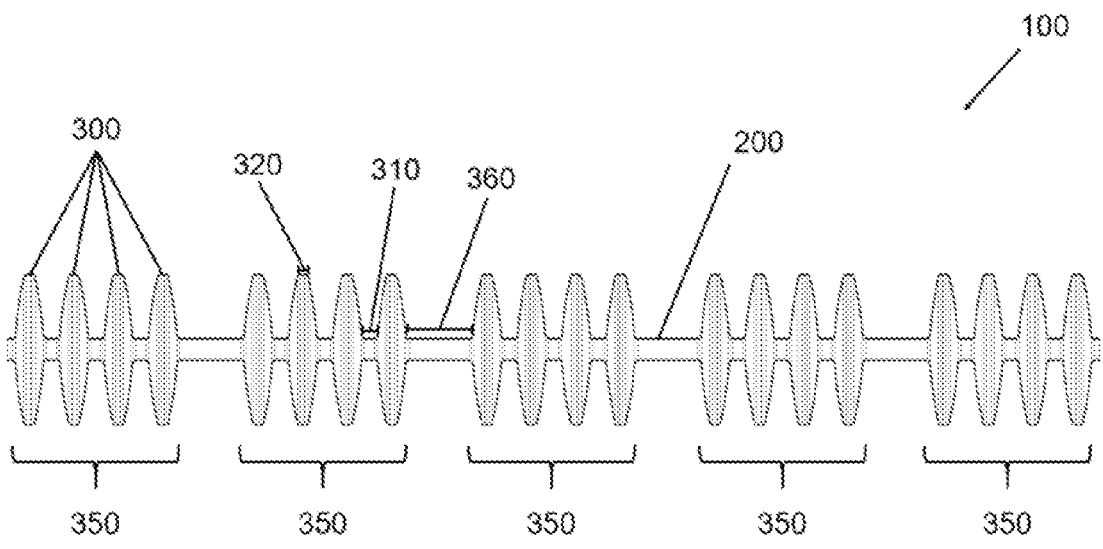
FIG. 1 is a schematic top view of a portion of an augmentation material 100. The augmentation material 100 comprises a wire 200 and, along the longitudinal axis of the wire 200, a plurality of groups 350 of axially adjacent connecting elements 300 (provided only by way of example with a reference sign) that extend radially from the wire 200, wherein only five of the groups 350 are shown in FIG. 1. Each of the groups 350 comprises four axially adjacent connecting elements 300 in the form of round, discus-like shaped disks which are arranged concentrically around the wire 200. The wire 200 and the connecting elements 300 are formed in one piece. Within a group 350, the axially adjacent connecting elements 300 have an axial connecting element spacing 310 (provided only by way of example with a reference sign) which corresponds approximately to one and a half times an axial connecting element extension 320 (provided only by way of example with a reference sign). The connecting element spacing 310 corresponds to the spacing between two axially adjacent connecting elements 300 of a group 350 at the level of the wire 200 and thus the distance of the wire 200 between these connecting elements 300. The axial connecting element extension 320 corresponds to the axial extension of the connecting elements 300 on the end of the connecting elements 300 radially facing away from the wire 200.

The individual groups 350 have an axial group spacing 360 (provided only by way of example with a reference sign) from one another which is three times the connecting element spacing 310. The axial group spacing 360 corresponds, analogously to the axial connecting element spacing 310, to the spacing between two axially adjacent groups 350 at the level of the wire and thus the distance of the wire 200 between these groups 350. The axial group spacing 360 enables a high flexibility of the augmentation device 100 and allows the shaping of a porous body made of the augmentation material 100.

Figure 2:
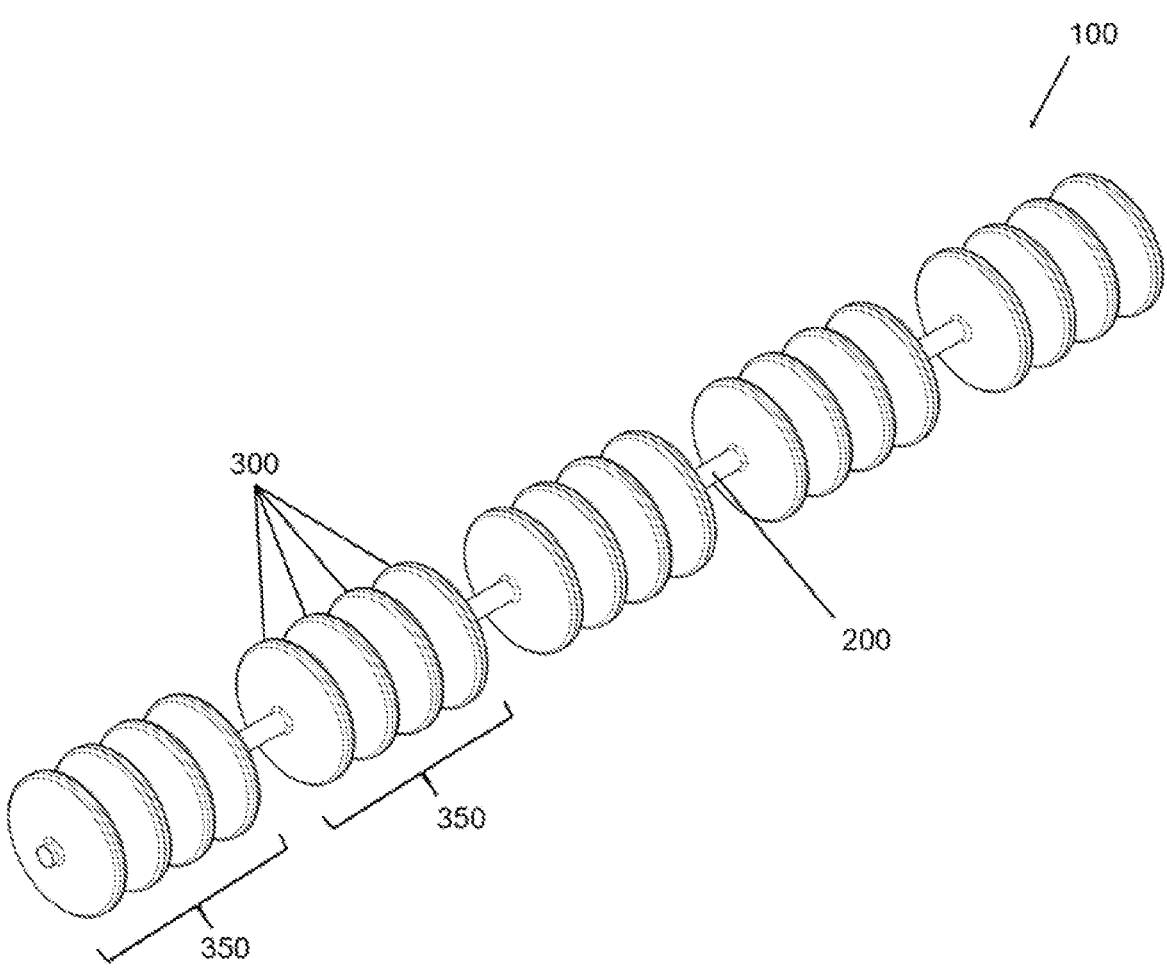

FIG. 2 shows the portion of the augmentation material 100 from FIG. 1 in a perspective side view.

Figure 3:
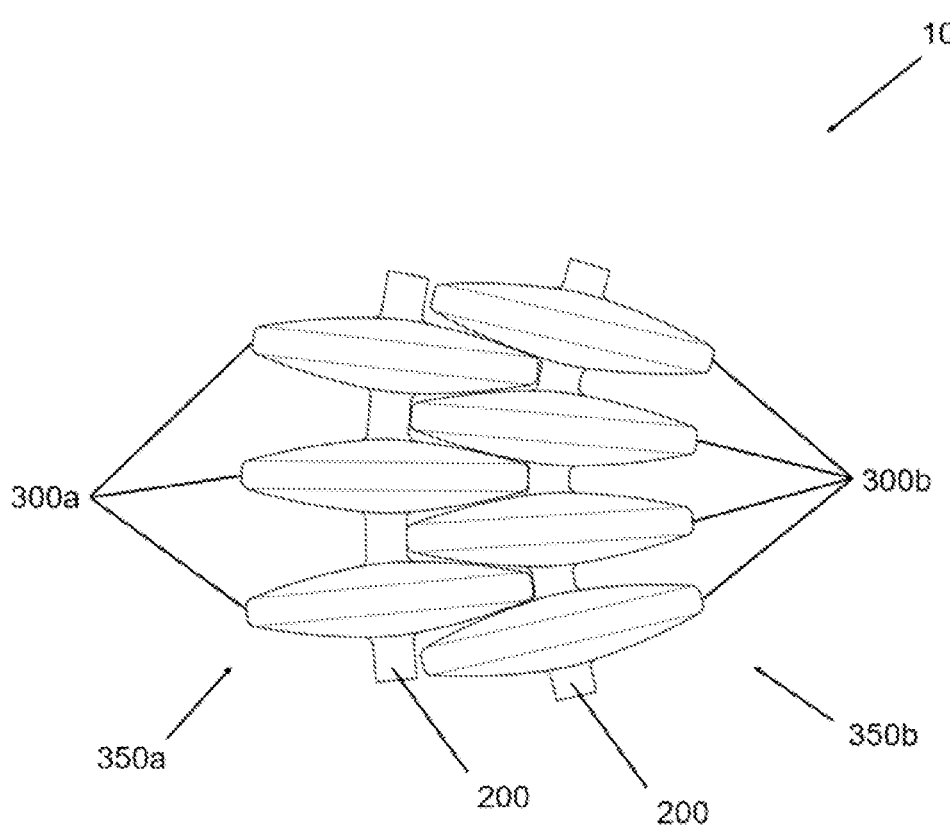

FIG. 3 is a further schematic top view of a portion of the augmentation material 100 from FIGS. 1 and 2, wherein the augmentation material 100 is shaped in such a way, in particular by deforming the wire 200, that a first group 350a of connecting elements 300a is connected in a positive-locking and friction-locking manner to a second group 350b of connecting elements 300b of the augmentation material 100.

Matching the connecting element spacing 310 (cf. FIG. 1) to the connecting element extension 320 (cf. FIG. 1) allows a positive-locking connection of the connecting elements 300a, 300b of the two groups 350a, 350b.

Connecting the two shown groups 350a, 350b as well as further groups (not shown) enables the formation of a porous body using the augmentation material 100. This porous body formed in this way from the augmentation material 100 can be used for filling cavities, in particular bone canals, and for forming a composite from the augmentation material 100 and a bone cement, in particular a PMMA bone cement.

Figure 4:
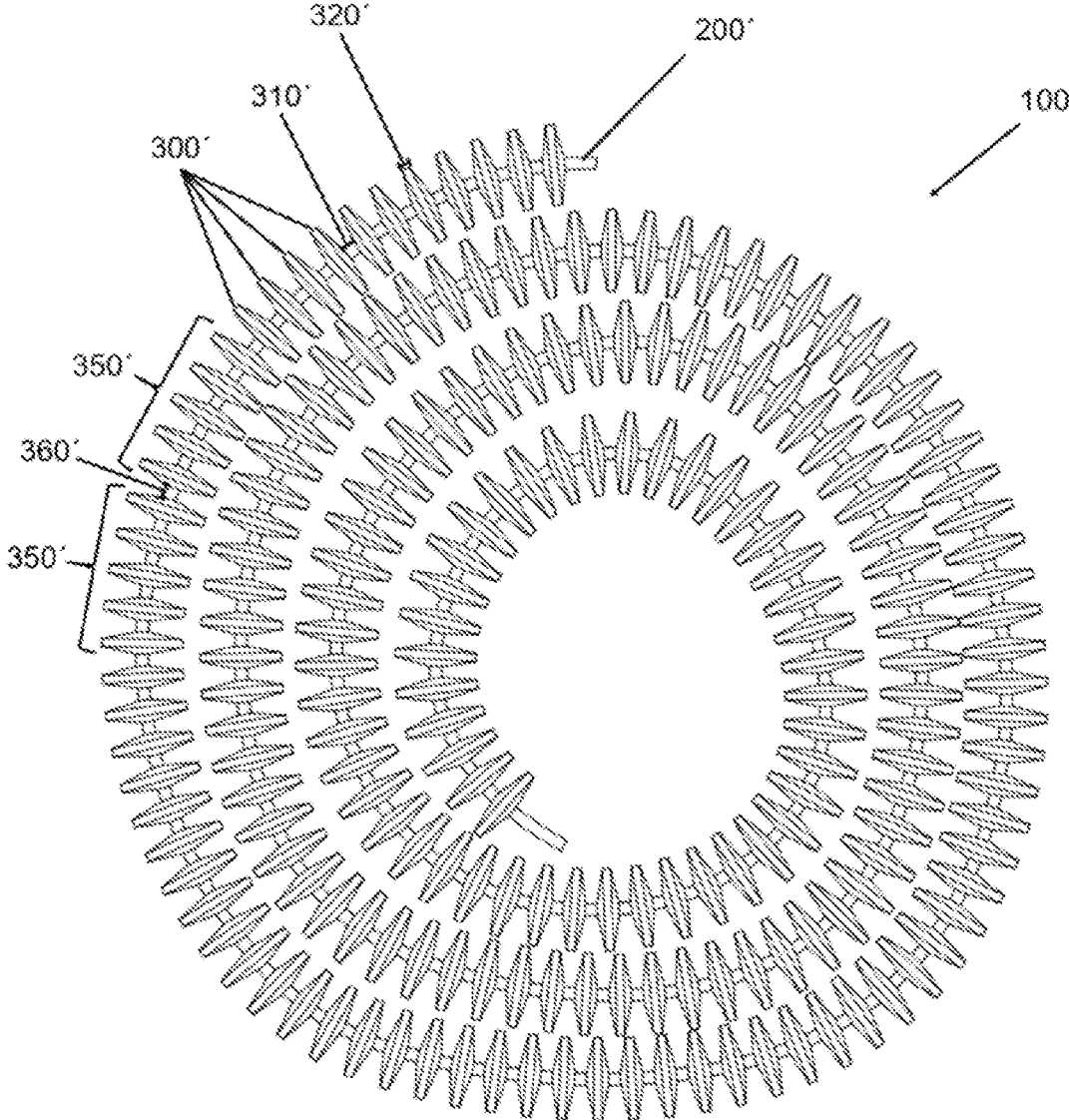

FIG. 4 is a schematic top view of a portion of a further embodiment of an augmentation material 100'. The embodiment of the augmentation material 100' largely corresponds to the embodiment described above and shown in FIGS. 1 to 3, and therefore reference is made to the above description to avoid repetition. Modifications of an embodiment shown in FIGS. 1 to 3 have the same reference sign with an additional apostrophe.

The axial group spacing 360' (provided only by way of example with a reference sign) of the groups 350' (provided only by way of example with a reference sign) of connecting elements 300' (provided only by way of example with a reference sign) of the augmentation material 100' corresponds to the axial connecting element spacing 310' (provided only by way of example with a reference sign) of connecting elements 300' within a group 350', so that the groups 350' appear to be a single large group of connecting elements 300'.

Figure 5:
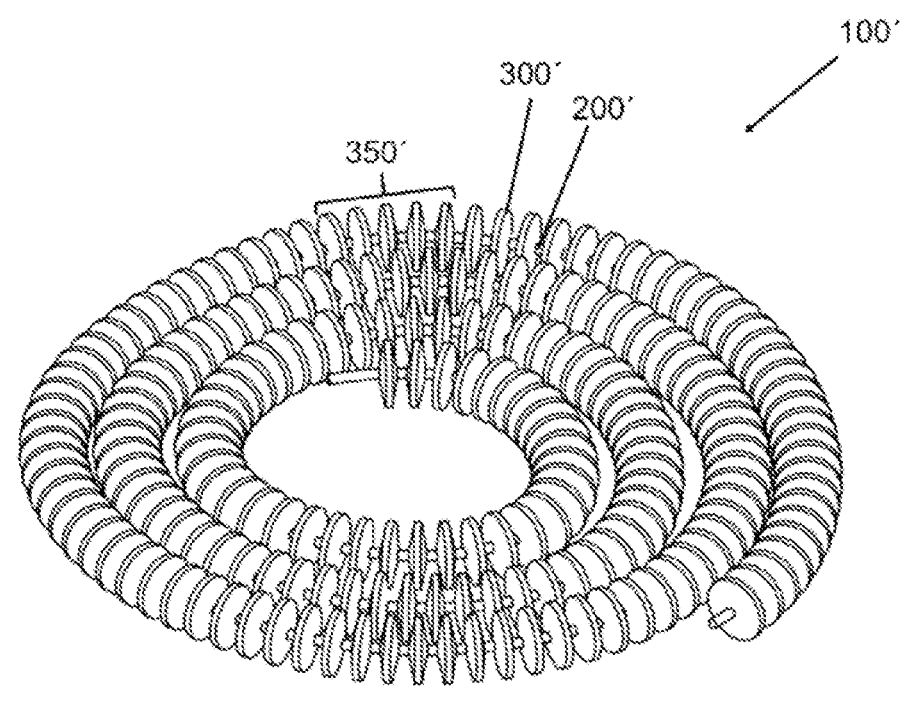

FIG. 5 shows the augmentation material 100' from FIG. 4 in a perspective side view.

Figure 6:
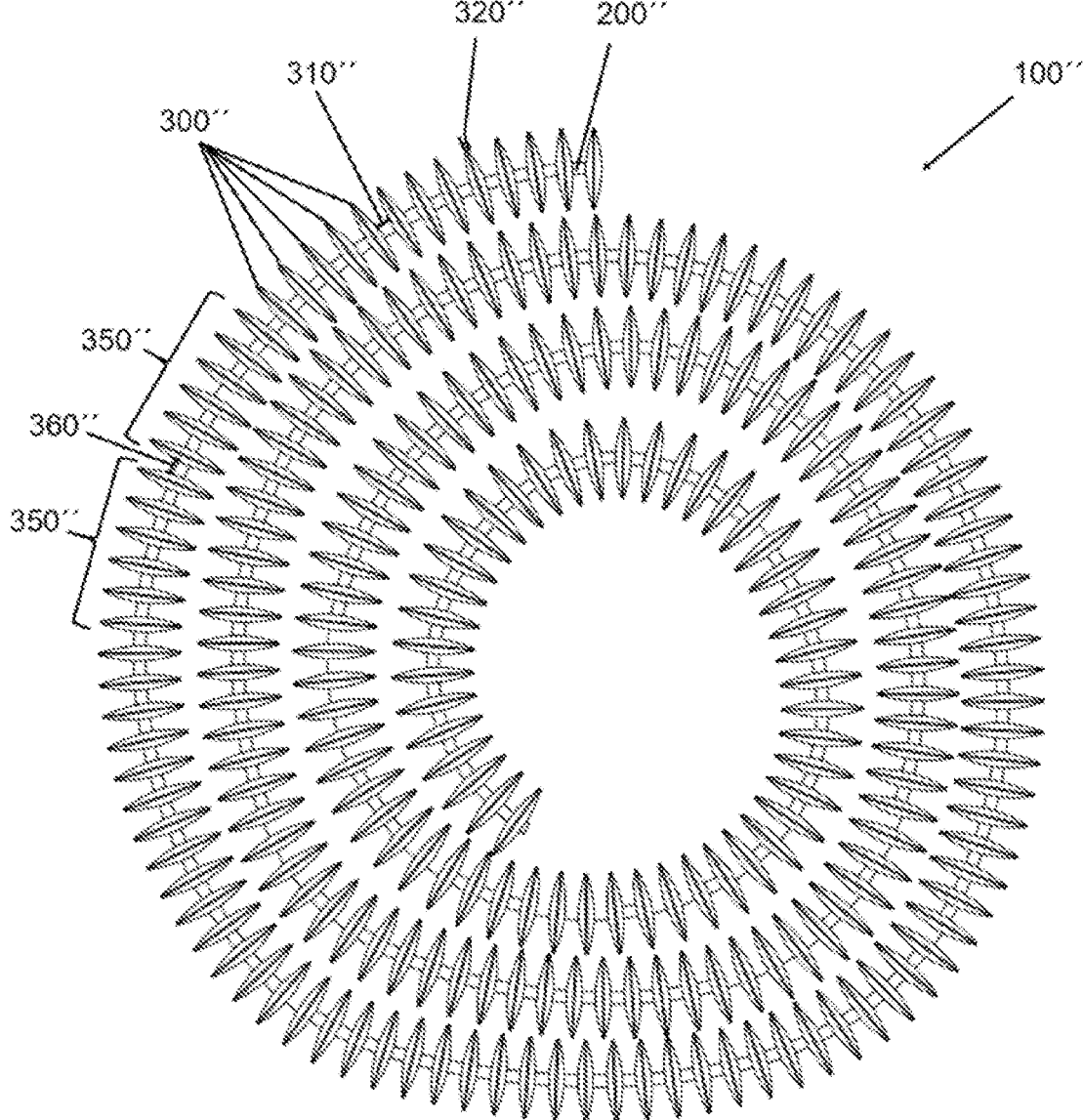

FIG. 6 is a schematic top view of a portion of a further embodiment of an augmentation material 100". The embodiment of the augmentation material 100" largely corresponds to the embodiments described above and shown in FIGS. 1 to 5, and therefore reference is made to the above description to avoid repetition. Modifications of any of the embodiments shown in FIGS. 1 to 5 have the same reference sign with two apostrophes.

Compared with the embodiment of the augmentation material 100' according to FIGS. 4 and 5, the embodiment shown in FIG. 6 has a smaller axial connecting element extension 320" (provided only by way of example with a reference sign) of the individual connecting elements 320".

Figure 7:
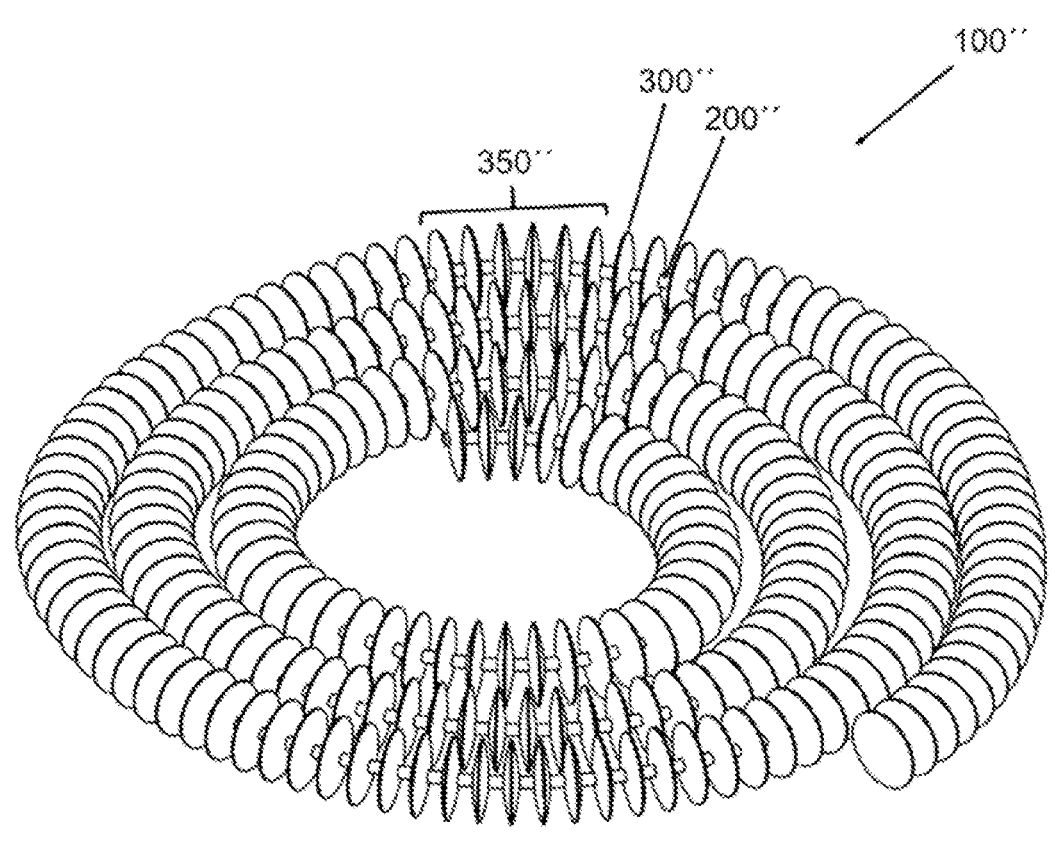

FIG. 7 shows the augmentation material 100" from FIG. 6 in a perspective side view.

Figure 8:
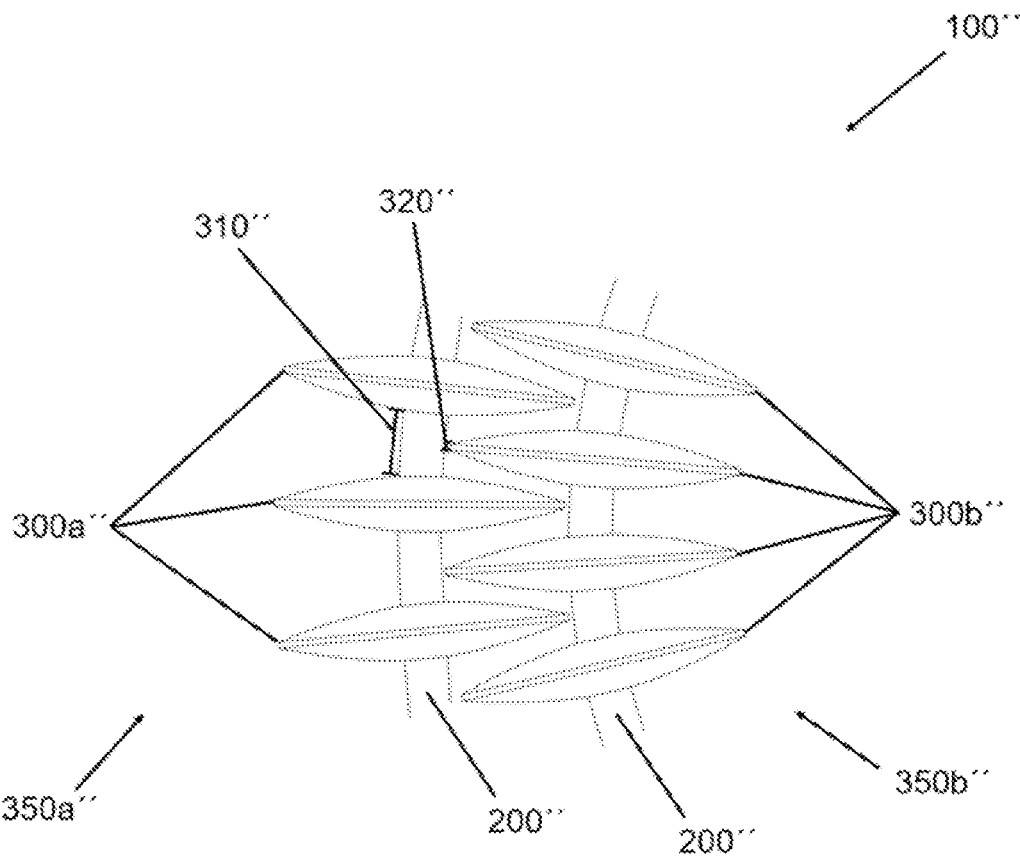

FIG. 8 is a further schematic top view of a portion of the augmentation material 100" from FIGS. 6 and 7, wherein the augmentation material 100" is shaped in such a way, in particular by deforming the wire 200", that a first group 350a" of connecting elements 300a" engages in a second group 350b" of connecting elements 300b" of the augmentation material 100" in order to connect the groups 350a", 350b" to one another in a friction-locking manner when the groups 350a", 350b" are displaced along the longitudinal axis of the wire 200". Because the axial connecting element extension 320" is small compared with the axial connecting element spacing 310", the groups 350a", 350b" do not form a positive-locking connection or only partially form one.

Figure 9:
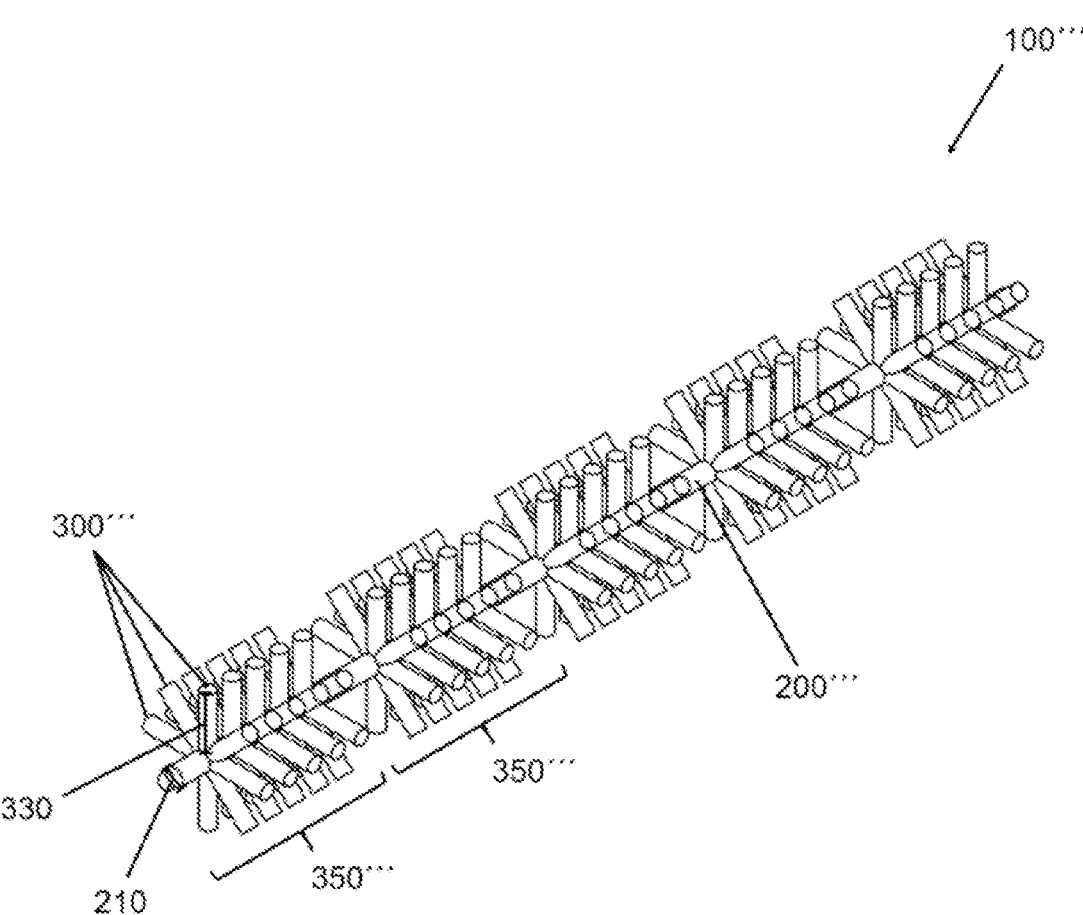

FIG. 9 is a top view of a portion of a further embodiment of an augmentation material 100'". The embodiment of the augmentation material 100'" largely corresponds to the embodiments described above and shown in FIGS. 1 to 8, and therefore reference is made to the above description to avoid repetition. Modifications of any of the embodiments shown in FIGS. 1 to 8 have the same reference sign with three apostrophes.

The connecting elements 300'" (provided only by way of example with a reference sign) of the embodiment according to FIG. 9 are shaped in the form of pins and not, as in the above embodiments according to FIGS. 1 to 8, in the form of disks. Each of the axially adjacent groups 350'" (provided only by way of example with a reference sign) of connecting elements 300'" in the form of pins comprises five axially adjacent pins, wherein each of these pins comprises an additional seven radially adjacent pins. Each of the groups 350'" thus comprises 40 connecting elements 300'" in the form of pins. A group 350'" thus comprises five subgroups of eight radially adjacent connecting elements 300''' in the form of pins, wherein the subgroups of eight radially adjacent pins extend radially from the wire 200''' in a cross-sectional plane of the wire 200''. In order to be able to effectively connect the connecting elements 300''' in the form of pins of two groups 350''' to one another in a friction-locking manner, the pins have a pin length 330 which corresponds to three times a wire diameter 210 of the wire 200'''. The individual groups 350'' are spaced apart from one another analogously to the augmentation material 100 of FIGS. 1 to 3.

Figure 10:
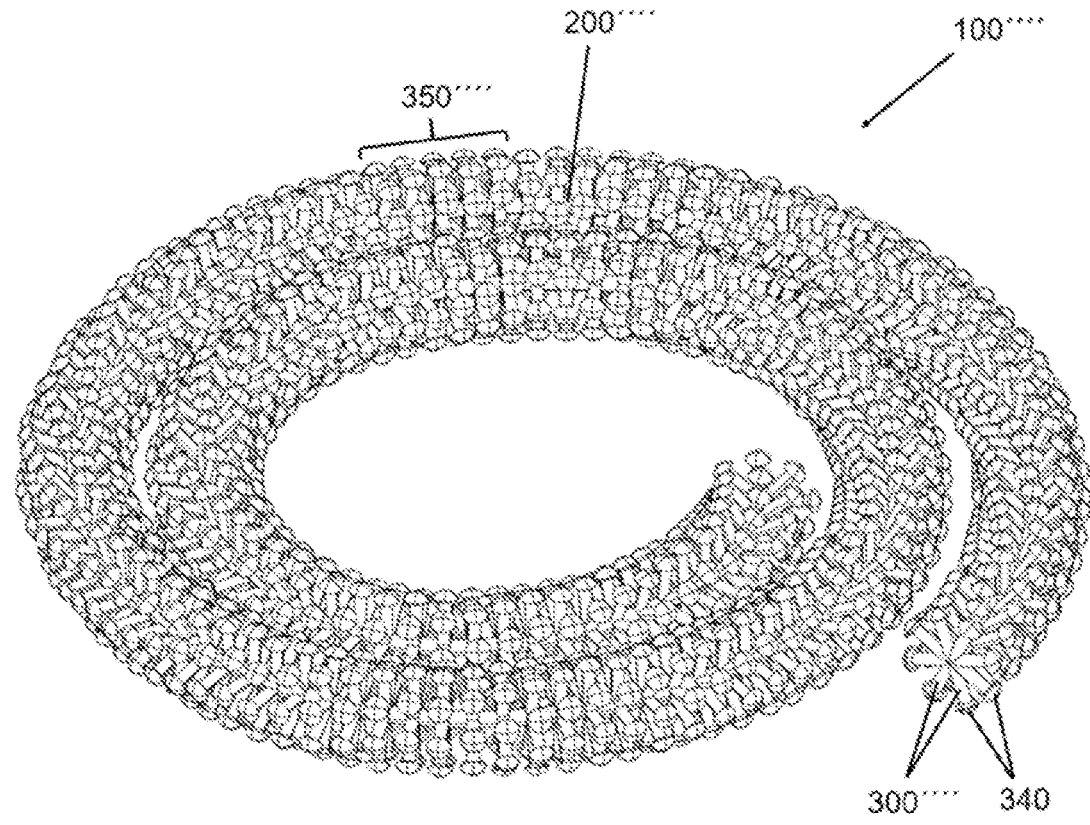

FIG. 10 is a perspective side view of another embodiment of an augmentation material 10''''. The embodiment of the augmentation material 100'''' largely corresponds to the embodiments described above and shown in FIGS. 1 to 9, and therefore reference is made to the above description to avoid repetition. Modifications of any of the embodiments shown in FIGS. 1 to 9 have the same reference sign with four apostrophes. The connecting elements 300''' (provided only by way of example with a reference sign) of the embodiment according to FIG. 10 are shaped in the form of pins, similar to the connecting elements according to the embodiment according to FIG. 9. The connecting elements 300'''' in the form of pins each comprise a mushroom 340 on an end opposite the wire. When two groups 350'''' of connecting elements 300'''' are pressed together, the mushrooms 340 snap together, so that the augmentation material 100'''' can form a very stable porous body.

Figure 11:
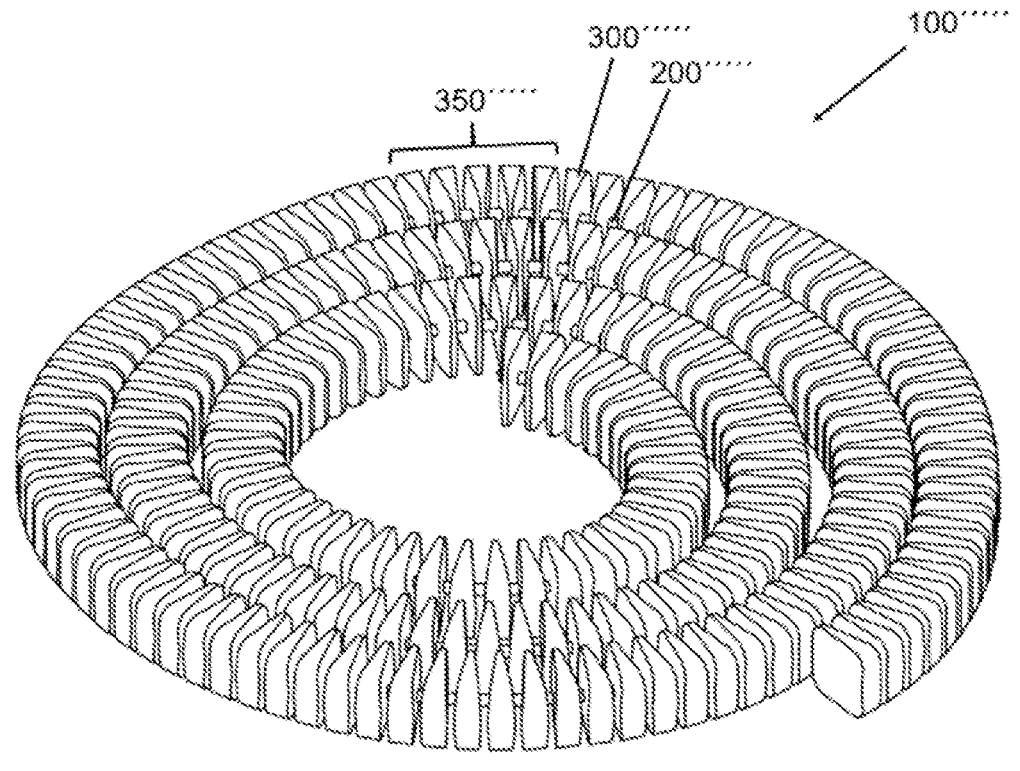

FIG. 11 is a perspective side view of another embodiment of an augmentation material 10'''''. The embodiment of the augmentation material 100''''' largely corresponds to the embodiments described above and shown in FIGS. 1 to 10, and therefore reference is made to the above description to avoid repetition. Modifications of any of the embodiments shown in FIGS. 1 to 10 have the same reference sign with five apostrophes. The connecting elements 300''''' are designed as wedge-shaped disks, so that a good friction-locking connection of the groups 350''''' is made possible when they are pressed together.

Figure 12:
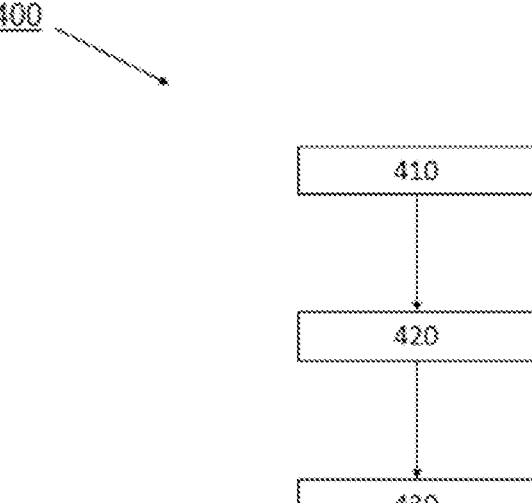

FIG. 12 is a flowchart of a method 400 for producing a composite comprising the augmentation material 100, 100', 100'', 100''', 100'''', 100''''' and a bone cement having the steps 410 to 430. The composite serves to fill a cavity.

In step 410, the augmentation material 100, 100', 100'', 100''', 100'''', 100''''' is provided in the form of a porous body which substantially corresponds to the shape of the cavity. For this purpose, the augmentation material 100, 100', 100'', 100''', 100'''', 100''''' can be shortened, for example by means of shears or pliers, so that the shape of the cavity can be reproduced as closely as possible. In order to form the shape of the cavity, it is preferred that two or more of the groups 350, 350', 350'', 350''', 350'''', 350''''' of connecting elements 300, 300', 300'', 300''', 300'''', 300''''' are pressed together such that they interact in a positive-locking and/or friction-locking manner and thus structurally stabilize the porous body made of augmentation material 100, 100', 100'', 100''', 100'''', 100'''''.

In step 420, a bone cement paste is applied into interspaces of the porous body shaped and provided from the augmentation material 100, 100', 100'', 100''', 100'''', 100''''' such that the interspaces are filled with bone cement paste and the augmentation material 100, 100', 100'', 100''', 100'''', 100''''' is encased in the bone cement paste.

In step 430, the bone cement paste encasing the porous body made of augmentation material 100, 100', 100'', 100''', 100'''', 100''''' cures to form the composite. The bone cement paste transitions into bone cement.

The composite produced in this way is inserted into the cavity to be filled, in particular a bone canal.

In one embodiment of the method 400, the provision 410 of the augmentation material 100, 100', 100'', 100''', 100'''', 100''''' takes place in the cavity to be filled, in particular a bone canal. The bone cement paste is applied in step 420 to the augmentation material 100, 100', 100'', 100''', 100'''', 100''''' in the form of a porous body such that the interspaces are filled with bone cement paste and the augmentation material 100, 100', 100'', 100''', 100'''', 100''''' is encased in the bone cement paste. The curing 430 of the bone cement paste to form the composite likewise takes place in the cavity to be filled.

| REFERENCE SIGNS | |
| --- | --- |
| 100, 100', 1000" 100''', 100'''', 100''''' | Augmentation material |
| 200, 200', 200" 200''', 200'''', 200''''' | Wire |
| 210 | Wire diameter |
| 300, 300', 300" 300''', 300'''', 300''''' | Connecting element |
| 300a | Connecting elements first group |
| 300b | Connecting elements further group |
| 310, 310', 310" | Axial connecting element spacing |
| 320, 320', 320" | Axial connecting element extension |
| 330 | Pin length |
| 340 | Mushroom |
| 350, 350', 350" 350''', 350'''', 350''''' | Group of connecting elements |
| 350a, 350a" | First group of connecting elements |
| 350b, 350b" | Further group of connecting elements |
| 360, 360', 360" | Axial group spacing |
| 400 | Method for producing a composite |
| 410 | Provision |
| 420 | Application |
| 430 | Curing |

The invention claimed is:

1. An implantable augmentation material comprising a wire and, in axial alignment along a longitudinal axis of the wire, a plurality of groups of axially adjacent connecting elements that extend radially from the wire, wherein the wire and the connecting elements are formed in one piece, wherein the connecting elements are formed as disks that extend radially from the wire, wherein the connecting elements are designed such that, when a first group from the plurality of groups is, by deforming the wire, pressed together with a further, non-axially adjacent group from the plurality of groups, the connecting elements of the two groups can be connected to one another in a positive-locking and/or friction-locking manner.

2. The augmentation material according to claim 1, wherein axially adjacent connecting elements in a group have an axial connecting element spacing from one another which corresponds to at least one axial connecting element extension of a connecting element along the longitudinal axis of the wire.

3. The augmentation material according to claim 1, wherein the disks are perforated and/or have an open-pore structure.

4. The augmentation material according to claim 1, wherein a group of connecting elements comprises 3 to 20 axially adjacent connecting elements.

5. The augmentation material according to claim 1, wherein axially adjacent groups of connecting elements have an axial group spacing (360) from one another which corresponds to at least twice the axial extension of a connecting element along the longitudinal axis of the wire.

6. The augmentation material according to claim 1, wherein the augmentation material is produced using a generative 3D printing method.

7. A composite comprising an augmentation material according to claim 1 and a PMMA bone cement, wherein the augmentation material is encased in the PMMA bone cement.

8. The composite according to claim 7, wherein the augmentation material in the composite occupies a volume fraction in the range of 30-70 percent by volume relative to the volume of the composite.

9. A method for producing a composite according to claim 7 for filling a cavity, comprising the steps of a. providing the augmentation material in an arrangement substantially corresponding to the shape of the cavity;

b. applying a bone cement paste in interspaces of the augmentation material such that the augmentation material is completely encased in the bone cement paste; and c. curing the bone cement paste to form the composite.

10. The method according to claim 9, wherein the augmentation material is provided in the cavity to be filled, and the application of the bone cement paste into the interspaces of the augmentation material and the curing of the bone cement paste takes place in the cavity.

* * * * *